US008057992B2

(12) United States Patent
Samoylova et al.

(10) Patent No.: US 8,057,992 B2
(45) Date of Patent: Nov. 15, 2011

(54) METHODS FOR IDENTIFYING PEPTIDES THAT BIND TO INTACT OOCYTES

(75) Inventors: Tatiana I. Samoylova, Auburn, AL (US); Henry J. Baker, Auburn, AL (US); Brenda Griffin, Ithaca, NY (US); Kristina Pendergrass, Tallassee, AL (US); Ludmila P. Globa, Auburn, AL (US); M. Daniel Givens, Auburn, AL (US); Kay P. Riddell, Auburn, AL (US); Nancy Cox, Auburn, AL (US)

(73) Assignee: Auburn University, Auburn, AL (US)

( * ) Notice: Subject to any disclaimer, the term of this patent is extended or adjusted under 35 U.S.C. 154(b) by 229 days.

(21) Appl. No.: 12/266,944

(22) Filed: Nov. 7, 2008

(65) Prior Publication Data

US 2009/0280137 A1   Nov. 12, 2009

Related U.S. Application Data

(60) Provisional application No. 61/002,340, filed on Nov. 8, 2007, provisional application No. 61/002,405, filed on Nov. 7, 2007, provisional application No. 61/002,413, filed on Nov. 7, 2007.

(51) Int. Cl.
*G01N 33/53* (2006.01)
(52) U.S. Cl. ............. 435/5; 435/7.1; 435/7.2; 435/7.21; 436/510; 530/853; 424/561; 424/811
(58) Field of Classification Search ........................ None
See application file for complete search history.

(56) References Cited

U.S. PATENT DOCUMENTS

| | | | |
|---|---|---|---|
| 6,383,496 B1 | 5/2002 | Curtiss et al. | |
| 6,923,958 B2 | 8/2005 | Xiang et al. | |
| 7,094,868 B2 | 8/2006 | Samoylova et al. | |

OTHER PUBLICATIONS

Engmann et al., Fertil Steril. Nov. 2005;84(5):1406-10.*
Suri, A. "Sperm-based contraceptive vaccines: current status, merits and development", Expert Reviews in Molecular Medicine, Sep. 12, 2005, vol. 7, Issue 18, 1-16.
Suri, A. "Contraceptive vaccines targeting sperm", Expert Opin. Biol. Ther., Mar. 2005, 5(3):381-392.
Naz, R.K. et al., "Recent advances in contraceptive vaccine development", Hum. Reprod. Advance Access, Aug. 19, 2005; 1-13.
Chamley, L.W., et al., "Antisperm antibodies and conception", Semin Immunopathol, 2007; 29:169-184.
Naz et al., "Identification of Human Sperm Peptide Sequence Involved in Egg Binding for Immunocontraception", Biology of Reproduction, 2000; 62:318-324.
Naz et al., "Human Sperm-Specific Peptide Vaccine That Causes Long-Term Reversible Contraception", Biology of Reproduction, 2002, 67:674-680.
Naz, "Human Synthetic Peptide Vaccine for Contraception Targeting Sperm", Archives of Andrology, 2004; 50:113-119.
Fayrer-Hosken et al., "Immunocontraception of African elephants" Nature 407: 149-150, 2000.
Paterson et al., "Immunocontraception with Zona pellucida Proteins", Cells Tissues Organs 2000, 166:228-232.
Wheir et al., "Immuno-Sterilization in Dogs Using Zona Pellucida (ZP)Based Vaccine", Proceedings of the Symposium on Nonsurgical Methods for Pet Population Control, Breckenridge, Colorado, Jun. 24-27, 2004.
Kehoe et al., "Filamentous Phage Display in the New Millenium", Chem. Rev. 2005, 105, 4056-4072.
Samoylova, Smith, "Identification of Cell Targeting Ligands Using Random Peptide-Presenting Phage Libraries". In Genetic Library Construction and Screening. Advanced Techniques and Applications. C. Bird and B. Smith, eds., Springer-Verlag, Heidelberg, pp. 209 231, 2002.
Samoylova et al., "Targeting peptides for microglia identified via phage display", Journal of Neuroimmunology, 127:13-21, 2002.
Baker et al., "Immunization of Cats and Dogs with an Anti-GnRH Protein Vaccine with Molecular Adjuvantation", Proceedings of the Symposium on Nonsurgical Methods for Pet Population Control, Breckemidge, Colorado, Jun. 24-27, 2004.
Wernette et al., "CpG oligodeoxynucleotides stimulate canine and feline immune cell proliferation", Veterinary Immunology and Immunopathology 2002; 84 : 223-236.
Fang et al., "The potential of phage display virions expressing malignant tumor specific antigen MAGE-AI epitope in murine model", Vaccine, 23, 4860-4866, 2005.
Gaubin et al., "Processing of Filamentous Bacteriophage Virions in Antigen-Presenting Cells Targets Both HLA Class I and Class II Peptide Loading Compartments" DNA Cell Bioloby, vol. 22(1):11-8, Nov. 1, 2003.
Yip et al., "Comparison of phage pIII, pVIII and GST as carrier proteins for peptide immunisation in Balb/c mice", Immunology Letters 79(3):197-202, 2001.
Dunbar et al., Isolation, Physicochemical Properties and Macromolecular Composition of Zona Pellucida from Porcine Oocytes:, Biochemistry 19, 1980: 356-365.
Smith "Filamentous Fusion Phage: Novel Expression Vectors that Display Cloned Antigens on the Virion Surface", Science 1985,228: 1315-1317.
Millar et al., "Vaccination with a Synthetic Zona Pellucida Peptide Produces Long-Term Contraception in Female Mice", Science 1989; 246: 935-938.
Ivanova et al., "Effect of Cryopreservation of Zona-Binding Capacity of Canine Spermatozoa In Vitro", Theriogenology 1999;52:163-170.
Hay et al., "Canine Spermatozoa Cryopreservation and Evaluation of Gamete Interaction", Theriogenology 48: 1329-1342, 1997.

(Continued)

*Primary Examiner* — Michael Szperka
(74) *Attorney, Agent, or Firm* — Andrus, Sceales, Starke & Sawall, LLP (57) ABSTRACT

Disclosed are methods, compositions, and zona pellucida binding peptides and polypeptides for use in immunocontraception of canines and other animals. The disclosed compositions may include pharmaceutical compositions. Methods for identifying peptides that bind to intact oocytes also are provided, in particular methods for identifying peptides that bind to zona pellucida of intact oocytes.

9 Claims, 5 Drawing Sheets

OTHER PUBLICATIONS

Mastromonaco et al., "The effects of oocyte storage and cumulus cell presence on canine zona penetration by domestic dog spermatozoa", Theriogenology 57: 1123-1134, 2002.

Naz et al., "Identification of Human Sperm Peptide Sequence Involved in Egg Binding for Immunocontraception," Biology of Reproduction, vol. 62, pp. 318-324, (2000).

Naz et al., "Human Sperm-Specific Peptide Vaccine that Causes Long-Term Reversible Contracept on," Biology of Reproduction, vol. 67, pp. 674-680, (2002).

O'Rand et al., "Inhibition of Fertility in Female Mice by Immunization with B-cell Epitope, the Synthetic Sperm Peptide, P10G," Journal of Reproductive Immunology, vol. 25, pp. 89-102, (1993).

Lea et al., "A Chimeric Sperm Peptide Induces Antibodies and Strain-Specific Reversible Infertility in Mice," Biology of Reproduction, vol. 59, pp. 527-536, (1998).

Naz et al., "Immunocontraceptive Effect of Izumo and Enhancement by Combination Vaccination," Molecular Reproduction and Development, vol. 75, pp. 336-344, (2008).

PCT Search Report, PCT/US2008/082800, European Patent Office, Apr. 2, 2009.

Conner et al., "Cracking the egg: increased complexity in the zona pellucida", Human Reproduction, Jan. 2005, 169(1):17-27.

Ditchkoff et al., "Ecology and management of feral hogs", Human-Wildlife Conflicts, 2007, 1(2):149-151.

Hammond et al., "Porcine adenovirus as a delivery system for swine vaccines and immunotherapeutics", Vet J, Jan. 2005, 169(1):17-27.

Hutton et al., "Disease risks associated with increasing feral swine numbers and distribution in the United States", Midwest Association of Fish and Wildlife Agencies, 2006.

Killian et al., "Immunocontraception of Florida feral swine with a single-dose GnRH vaccine", American Journal of Reproductive Immunology, 2006, 55:378-384.

Miller et al., "Immunocontraception of white-tailed deer with GnRH vaccine", American Journal of Reproductive Immunology, 2000, 44(5):266-274.

Shata et al., "Recent advances with recombinant bacterial vaccine vectors", Molec. Med. Today, Feb. 1, 2000, 6(2):66-71.

Szardenings et al., "Phage Display Selection on Whole Cells Yields a Peptide Specific for Melanocortin Receptor 1", Journal of Biological Chemistry, Oct. 31, 1997, 272(44):27943-27948.

"Lab FAQs: Find a Quick Solution", 3rd Edition, published by Roche Applied Science, https://www.roche-applied-science.com/PROD__INF/MANUALS/labfaqs/lab__faqs.pdf, available Mar. 22, 2011.

Brown et al., "A single administration immunocontraceptive vaccine for grey seals", Nature, 1996, 379:30-31.

Daudel et al., "Use of attenuated bacteria as delivery vectors for DNA vaccines", Expert Review of Vaccines, 2007, 6(1):97-110.

Garmory et al., "The Use of Live Attenuated Bacteria as a Delivery System for Heterologous Antigens", Journal of Drug Targeting, 2003, 11(8-10):471-479.

Gentschev et al., "Recombinant attenuated bacteria for the delivery of subunit vaccines", Vaccine, 2001, 19:2621-2628.

Harris, "Swine ZP and Dog Immunocontraception", Proceedings of the Symposium on Nonsurgical Methods for Pet Population Control, Jun. 24-27, 2004.

Jewgenow et al., "Antigenic and Antifertile Determinants of Feline Zona Pellucida B Protein—A Strategy for Contraceptive Vaccine Development", Proceedings of the Symposium on Nonsurgical Methods for Pet Population Control, Jun. 24-27, 2004.

* cited by examiner

METHODS FOR IDENTIFYING PEPTIDES THAT BIND TO INTACT OOCYTES

CROSS-REFERENCE TO RELATED APPLICATIONS

The present application claims the benefit of priority under 35 U.S.C. §119(e) to U.S. provisional application No. 61/002,405, filed on Nov. 7, 2007; U.S. provisional application No. 61/002,413, filed on Nov. 7, 2007; and U.S. provisional application No. 61/002,340, filed on Nov. 8, 2007; the contents of which are incorporated herein by reference in their entireties.

BACKGROUND

The present subject matter relates to the fields of peptide and polypeptide selection, immunology, and contraception in animals. In particular, the present subject matter relates to peptides and polypeptides that bind to the zona pellucida (ZP) of oocytes (e.g., canine oocytes), methods for selecting such peptides and polypeptides, and pharmaceutical compositions that comprise such peptides and polypeptides (e.g., for inducing an immune response against sperm). The pharmaceutical compositions may include immunogenic compositions and vaccines that may be administered to animals such as canines for immunocontraception.

"Capture and kill," the primary strategy used to control unwanted dog populations, has not reduced the magnitude of this serious problem in 100 years because it illogically addresses the result rather than the cause of the problem. The obvious solution is preventing the birth of unwanted animals. Surgical gonadectomy is considered the gold standard and low cost spay/neuter clinics have made limited progress in reducing unwanted dog populations in some locals, but it is not equal to this overwhelming task. Clearly, an effective, technically uncomplicated and inexpensive method applied on a mass scale is needed. In spite of recurring claims for new wonder drugs, none have met the challenge. For example, the current attention is focused on an industrial chemical (vinylcyclohexene dioxide) which kills primordial cells of ovarian follicles. Unfortunately, based on tests of the National Toxicology Program of the National Institute of Environmental Health Sciences, The International Agency for Research on Cancer (IARC) of the World Health Organization has classified this chemical as a carcinogen, and its production has been discontinued world wide. Some chemical, hormonal and vaccine contraceptive strategies have had limited success, and likely solutions will come from incremental improvement of these proven technologies. Zona pellucida (ZP) derived from pig ovaries (pZP) has been studied as an antigen for contraceptive vaccines for decades and shown to be highly successful for some species, but it is highly variable and frequently ineffective in dogs. Here, using powerful, cutting edge phage display technology, we isolate canine specific zone pellucida (cZP) binding peptides for use as antigens in immunogenic compositions and vaccines to block fertilization in dogs.

SUMMARY

Disclosed are methods, compositions, and zona pellucida binding peptides and polypeptides for use in immunocontraception of canines and other animals. The disclosed compositions may include pharmaceutical compositions. The disclosed compositions may include genetically modified biological vectors (e.g., viral or bacterial vectors), that after administration to an animal, express an encoded contraceptive peptide, which in turn, stimulates production of antipeptide antibodies with contraceptive properties.

The disclosed methods include methods for identifying a peptide or polypeptide that binds to the zona pellucida of intact oocytes (e.g., canine oocytes). The methods may include: (a) isolating oocytes; (b) contacting the oocytes with a phage library; (c) selecting phage that bind to the oocytes, thereby identifying peptides that bind to the zona pellucida of the intact oocytes. In the disclosed methods, the phage library may be contacted with a relatively small number of oocytes (e.g., less than about 1000 oocytes).

In some embodiments, the identified peptides or polypeptides may include an amino acid sequence selected from a group consisting of SEQ ID NO:1 (LNSFLRS), SEQ ID NO:2 (LSTALRS), SEQ ID NO:3 (SSWYRGA), SEQ ID NO:4 (TGTSTRA), SEQ ID NO:5 (YLPIYTIPSMVY), SEQ ID NO:6 (NNQSPILKLSIH), SEQ ID NO:7 (AHPNTAPIHPKF), SEQ ID NO:8 (CLNSFLRSC), SEQ ID NO:9 (CLNSFLRSCKGG), SEQ ID NO:10 (CSSWYRGAC), SEQ ID NO:11 (CSSWYRGACKGGY), SEQ ID NO:12 (YLPIYTIPSMVYGG), and SEQ ID NO:13 (NNQSPILKLSIHGG). Also disclosed are polynucleotides encoding the identified peptides or polypeptides. The polynucleotide may be operably linked to a promoter sequence as a recombinant polynucleotide. The recombinant polynucleotide may be present in a vector which is utilized to transform an isolated cell. The encoded peptide or polypeptide may be produced by a method that includes: a) culturing the transformed cell under conditions suitable for expression of the polypeptide; and b) recovering the polypeptide so expressed. Alternatively, the peptide may be prepared by a synthetic method.

The identified peptides or polypeptides may be utilized as antigens. In some embodiments, the identified peptides or polypeptides may be modified to enhance antigenicity. For example, the peptides or polypeptides may be conjugated to a carrier protein or an immunogenic molecule (e.g., keyhole-limpet hemocyanin (KLH)).

The disclosed pharmaceutical composition may include immunogenic compositions or vaccine compositions. In some embodiments, the compositions include (a) one or more polypeptides comprising an amino acid sequence selected from a group consisting of SEQ ID NO:1 (LNSFLRS), SEQ ID NO:2 (LSTALRS), SEQ ID NO:3 (SSWYRGA), SEQ ID NO:4 (TGTSTRA), SEQ ID NO:5 (YLPIYTIPSMVY), SEQ ID NO:6 (NNQSPILKLSIH), SEQ ID NO:7 (AHPNTAPIHPKF), SEQ ID NO:8 (CLNSFLRSC), SEQ ID NO:9 (CLNSFLRSCKGG), SEQ ID NO:10 (CSSWYRGAC), SEQ ID NO:11 (CSSWYRGACKGGY), SEQ ID NO:12 (YLPIYTIPSMVYGG), SEQ ID NO:13 (NNQSPILKLSIHGG), and SEQ ID NO:14 (YLPVGGLRRIGG); and (b) a suitable excipient, carrier, or diluent. For example, the compositions may include two or more polypeptides, where each of the two or more polypeptides comprise an amino acid sequence selected from a group consisting of SEQ ID NO:1 (LNSFLRS), SEQ ID NO:2 (LSTALRS), SEQ ID NO:3 (SSWYRGA), SEQ ID NO:4 (TGTSTRA), SEQ ID NO:5 (YLPIYTIPSMVY), SEQ ID NO:6 (NNQSPILKLSIH), SEQ ID NO:7 (AHPNTAPIHPKF), SEQ ID NO:8 (CLNSFLRSC), SEQ ID NO:9 (CLNSFLRSCKGG), SEQ ID NO:10 (CSSWYRGAC), SEQ ID NO:11 (CSSWYRGACKGGY), SEQ ID NO:12 (YLPIYTIPSMVYGG), and SEQ ID NO:13 (NNQSPILKLSIHGG). The immunogenic compositions or vaccine compositions may further include an adjuvant (e.g., aluminum hydroxide). The immunogenic compositions or vaccine compositions further may include an immunostimulatory agent (e.g., an immunostimulatory oligodeoxynucleotide such as CpG).

Also disclosed are methods for using the peptides, polypeptides, or compositions that contain the peptides or polypeptides. The disclosed methods may include administering the disclosed immunogenic compositions or vaccine compositions to an animal in order to induce an immune response (e.g., an anti-sperm antibody response, a T-cell response, or both). The disclosed methods may include methods for producing antibodies that bind to sperm (e.g., anti-canine sperm antibodies). In the methods, the compositions may be administered to an animal of either sex (i.e., female or male). The methods further may include isolating the induced antibodies from a sample obtained from the animal (e.g., from blood or a blood product such as serum or plasma).

The disclosed methods also may include methods for immunizing an animal against conception (i.e., immunocontraceptive methods). The methods may include administering the disclosed immunogenic composition or vaccine compositions to an animal (e.g., a female or male canine), thereby immunizing the animal against conception. In some embodiments, the animal is immunized for a temporary period of time (e.g., for a period of weeks or months).

DETAILED DESCRIPTION

The disclosed subject matter is further described below.

Unless otherwise specified or indicated by context, the terms "a", "an", and "the" mean "one or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean plus or minus $\leq$10% of the particular term and "substantially" and "significantly" will mean plus or minus >10% of the particular term.

As used herein, the terms "include" and "including" have the same meaning as the terms "comprise" and "comprising."

The terms "subject" and "patient" may be used interchangeably herein. A patient or subject may refer to a non-human patient or subject at risk for conception (e.g., a canine).

The term "sample" is used in its broadest sense. A sample may comprise a bodily fluid (e.g., blood or a blood product such as serum or plasma obtained from a subject or patient).

As used herein, the term "amino acid sequence" refers to an oligopeptide, peptide, polypeptide, or protein sequence, or a fragment of any of these, and to naturally occurring or synthetic molecules. The terms "peptide" and "polypeptide" may be used interchangeably herein. Generally, the term "peptide" refers to an amino acid polymer having a relatively low number of amino acid residues (e.g., no more than about 50, 40, 30, 20, 15, 12, or 7 amino acid residues). For the most part, peptides will comprise at least about 7 to about 50 amino acids, preferably at least about 7 to about 30 amino acids, more preferably about 7 to about 8, 9, 10, 11, 12, 13, 14, 15, 16, 17, 18, 19, or 20 amino acids. Generally, the term "polypeptide" refers to an amino acid polymer having a greater number of amino acid residues than a peptide. The term "protein" also may be used herein interchangeably with the term "polypeptide."

The presently disclosed peptides may be synthetic. As used herein, "synthetic peptide" refers to a peptide which has an amino acid sequence which is not a native sequence or is not in its native context and which confers on phage displaying it the ability to bind or preferentially bind to a particular cell population. By "not in its native context" is intended that the peptide is substantially or essentially free of amino acid sequences that naturally flank the amino acid sequence of the peptide in the native protein which comprises the amino acid sequence of the peptide. For example, a synthetic peptide which is not in its native context may be flanked at either or both ends by no more than 50, 40, 30, 20, 10, 9, 8, 7, 6, 5, 4, 3, 2, or 1 amino acid(s) found in the native protein.

The peptides and polypeptides disclosed herein may exhibit at least two-fold, three-fold, four-fold, five-fold, six-fold, seven-fold, ten-fold, twenty-fold, thirty-fold or more increased binding affinity for ZP of canine oocytes relative to at least one category or type of other cell. Peptides and polypeptide that exhibit such binding characteristics are said to exhibit preferential binding to ZP. Peptides and polypeptides that do not exhibit at least a two-fold increased binding affinity for ZP relative to another category or type of other cell but that bind to ZP are simply said to bind to ZP.

As used herein, the term "nucleic acid sequence" refers to a nucleotide, oligonucleotide, polynucleotide, or any fragment thereof. As used herein, the term "polynucleotide" refers to a nucleotide polymer. A polynucleotide may encode a peptide or polypeptide as disclosed herein. A polynucleotide may be operably linked to a heterologous promoter sequence as a recombinant polynucleotide. "Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame. A recombinant polynucleotide comprising a polynucleotide operably linked to a promoter sequence may be present in a vector (e.g., a plasmid) which may be utilized to transform a host cell (e.g., where the vector further includes a selectable marker).

The presently disclosed peptides and polypeptide may be isolated or substantially purified. The terms "isolated" or "substantially purified" refers to peptides or polypeptides that are removed from their natural environment and are isolated or separated, and are at least 60% free, preferably at least 75% free, and most preferably at least 90% free from other components with which they are naturally associated.

Disclosed are methods for isolating peptides and polypeptides that bind to the ZP of intact oocytes, in particular, intact canine oocytes. The disclosed methods are related to phage display methods known in the art (see, e.g., U.S. Pat. No. 7,094,868, which discloses isolating peptides by phage display, the content of which is incorporated herein by reference in its entirety). The disclosed methods may include: (a) isolating intact oocytes (e.g., canine oocytes); (b) contacting the oocytes with a phage library; (c) selecting phage that bind to the oocytes, thereby identifying peptides that bind to the ZP of the oocytes. Surprisingly, in the disclosed methods, the phage library may be contacted with a relatively small number of oocytes (e.g., less than about 1000 oocytes). It is generally understood in the field of phage display technology that a significant number of cells (typically millions) are needed for successful selection of cell-binding peptides on intact cells. This significant number of cells is easily achievable for the vast majority of cell types via propagation in cell culture media. However, oocytes cannot be obtained through cell culturing and oocytes with surrounding ZP should be isolated directly from ovaries removed from animals. Only 20-30 oocytes can be isolated from one canine ovary. As such, thousands of animals would be require in order to obtain the required number (millions) of oocytes for phage display selection protocols commonly in use. In addition to the huge numbers of animals needed for isolating a sufficient number of oocytes, the oocyte isolation procedure is very time consuming and takes at least 4-5 hours for an experienced technician to isolate 100 oocytes. Thus, it would take thousands of animals and years of work to isolate the number of oocytes required by currently accepted protocols. For these reasons, millions of oocytes cannot be readily available for the use in phage display selection protocols that are generally utilized in the field. Therefore, herein a phage display selection procedure that requires no more than 1000 oocytes surrounded by ZP was developed.

Also disclosed are peptide and polypeptides identified by the phage display method. Peptides identified herein include peptides having the amino acid sequence of SEQ ID NOs:1-13. Also disclosed are polypeptides comprising the amino acid sequence of any of SEQ ID NOs:1-13, polynucleotides encodings such polypeptides, recombinant polynucleotides comprising such polynucleotides, expression vectors, and methods for expressing the encoded polypeptide.

The peptides disclosed herein may be fused (e.g., genetically in frame) or conjugated (e.g., chemically) to other peptides or non-peptide moieties (e.g., in order to provide an antigen). For example, a fusion polypeptide as contemplated herein may include a fusion of any of the peptides of SEQ ID NO:1-13 and another immunogenic peptide. The peptides disclosed herein may be present in a polypeptide (e.g., where the polypeptide comprises one or more copies of the amino acid sequence of the peptide, optionally in tandem). In some embodiments, a fusion polypeptide as contemplated herein may include a fusion of any of the peptides of SEQ ID NO:1-3 and a carrier protein. The disclosed peptides may be modified to enhance immunogenicity. For example, the peptides disclosed herein may be conjugated to a carrier protein or an immunogenic molecule (e.g., keyhole-limpet hemocyanin).

The disclosed methods may include inducing an immune response against one or more peptides that bind to the ZP. In some embodiments, the methods include inducing polyclonal antibodies against one or more peptides that bind to the ZP by administering to an animal an immunogenic composition that includes one or more of the peptides. The animal may be a non-human animal (e.g., a canine). The induced polyclonal antibodies may include anti-sperm antibodies. The methods disclosed herein also may include preventing conception by administering to the animal an immunogenic composition that includes one or more peptides that bind to the ZP. For example, an animal (e.g., a non-human animal such as a canine) may be protected against conception by administering to the animal a composition that includes one or more peptides that bind to the ZP together with a suitable excipient, carrier, or diluent.

Also disclosed are pharmaceutical compositions which may include immunogenic compositions and vaccines for performing the disclosed methods. An immunogenic composition may be monovalent or polyvalent. Typically, the immunogenic compositions include one or more peptides that bind to the ZP together with a suitable excipient, carrier, or diluent. The immunogenic compositions may include one or more polypeptides comprising the amino acid sequence of a peptide as disclosed herein, for example one or more polypeptides comprising the amino acid sequence of any of SEQ ID NOs:1-13. In some embodiments, the immunogenic compositions may include two or more polypeptides where each polypeptide of the two or more polypeptides comprises the amino acid sequence of any of SEQ ID NOs:1-13. The immunogenic compositions may include an isolated polypeptide or peptide at a concentration sufficient to induce an immunogenic response against canine sperm (e.g., via antibody induction, a T-cell response, or both). In some embodiments, the immunogenic compositions may include at least about 10 μg of the isolated polypeptide or peptide (or preferably, at least about 100 μg of the isolated polypeptide or peptide).

The "immunogenic compositions" and "vaccines" disclosed herein are capable of stimulating an immune response in an animal inoculated with the immunogenic composition or vaccine. An immune response may include induction of antibodies, induction of a T-cell response, or both. Herein, the term "prevention" when used in reference to an immunogenic composition or vaccine may refer to the partial or complete prevention against conception via an immune response induced by the immunogenic composition or vaccine.

An "an immunogenic composition comprising a given peptide or polypeptide" refers to a composition containing the given peptide or polypeptide. The composition may comprise a dry formulation or an aqueous solution. An "immunogenic peptide or polypeptide" is an antigen which is capable of eliciting an immune response when introduced into an animal, for example, a canine.

The methods disclosed herein may include administering an immunogenic composition or a vaccine to an animal. An "animal," as used herein, may include a non-human animal (e.g., a canine).

The methods disclosed herein also may include protecting an animal against conception or preventing an animal from conceiving by administering to the animal a composition that includes an isolated peptide as disclosed herein. The administered composition may include an immunogenic composition or a vaccine. For example, an animal (e.g., a canine) may be protected against conception by administering to the animal a composition that includes an isolated polypeptide comprising an amino acid sequence of any of SEQ ID NOs:1-13 and a suitable excipient, carrier, or diluent.

The presently disclosed peptide or polypeptide may be expressed by viral vectors or bacterial vectors (e.g., as part of an immunogenic composition or vaccine). As used herein, a "viral vector" (e.g., an adenovirus, Sendai virus, or measles virus vector) refers to recombinant viral nucleic acid that has been engineered to express a heterologous polypeptide. The recombinant viral nucleic acid typically includes cis-acting elements for expression of the heterologous polypeptide. The recombinant viral nucleic acid typically is capable of being packaged into a helper virus that is capable of infecting a host cell. For example, the recombinant viral nucleic acid may include cis-acting elements for packaging. Typically, the viral vector is not replication competent or is attenuated. An "attenuated recombinant virus" refers to a virus that has been genetically altered by modern molecular biological methods (e.g., restriction endonuclease and ligase treatment, and rendered less virulent than wild type), typically by deletion of specific genes. For example, the recombinant viral nucleic acid may lack a gene essential for the efficient production or essential for the production of infectious virus. Recombinant attenuated bacteria also may be utilized as vectors in the pharmaceutical compositions and vaccines disclosed herein (e.g., recombinant attenuated Shigella, Salmonella, Listeria, or Yersinia). Recombinant bacterial vaccine vectors are described in Daudel et al, "Use of attenuated bacteria as delivery vectors for DNA vaccines," Expert Review of Vaccines, Volume 6, Number 1, February 2007, pp. 97-110(14); Shata et al., "Recent advances with recombinant bacterial vaccine vectors," Molec. Med. Today (2000), Volume 6, Issue 2, 1 Feb. 2000, pages 66-71; Clare & Dougan, "Live Recombinant Bacterial Vaccines," Novel Vaccination Strategies, Apr. 16, 2004 (Editor Stefan H. E. Kaufman); Gentschev et al., "Recombinant Attenuated Bacteria for the Delivery of Subunit Vaccines," Vaccine, Volume 19, Issues 17-19, 21 Mar. 2001, Pages 2621-2628; Garmory et al., "The use of live attenuated bacteria as a delivery system for heterologous antigens," J. Drug Target. 2003; 11 (8-10):471-9; U.S. Pat. No. 6,383,496; and U.S. Pat. No. 6,923,958 (which all are incorporated by reference herein in their entireties).

The immunogenic compositions or vaccines may be formulated for delivery in any suitable manner. For example, the immunogenic compositions or vaccines may be formulated for at least one of intramuscular delivery, subdermal delivery, subcutaneous delivery, oral delivery, intravenous delivery, intraperitoneal delivery, and intranasal delivery. The immunogenic compositions or vaccines can be administered using a variety of methods including intranasal and/or parenteral (e.g., intramuscular) administration. In some embodiments of the methods, the immunogenic composition or vaccine is administered intramuscularly one or more times at suitable intervals (e.g., at intervals of 2-4 weeks), followed by administration of the immunogenic composition or vaccine at least once intramuscularly or intranasally after a suitable time period (e.g., 2-4 weeks after the last parenteral administration of vaccine). The immunogenic compositions or vaccines may be administered to an animal of either sex (i.e., female or male).

The present immunogenic composition and vaccines may be formulated with a pharmaceutically or veterinarily acceptable excipient, carrier, or diluent. The forms suitable for injectable commonly include sterile aqueous solutions (where water soluble) or dispersions and sterile powders for the extemporaneous preparation of sterile injectable solutions or dispersion. The formulation should desirably be sterile and fluid to the extent that easy syringability exists. The dosage form should be stable under the conditions of manufacture and storage and typically is preserved against the contaminating action of microorganisms such as bacteria and fungi. The carrier can be a solvent or dispersion medium containing, for example, water, ethanol, polyol (for example, glycerol, propylene glycol, liquid polyethylene glycol, and the like), suitable mixtures thereof and vegetable oils. One possible carrier is a physiological salt solution. The proper fluidity of the solution can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal (sodium ethylmercuri-thiosalicylate), deomycin, gentamicin and the like. In many cases it may be preferable to include isotonic agents, for example, sugars or sodium chloride. Prolonged absorption of the injectable compositions, if desired, can be brought about by the use in the compositions of agents delaying absorption, for example, aluminum monostearate and gelatin.

The present immunogenic composition or vaccines may include an adjuvant. For example, adjuvants may include aluminum hydroxide, aluminum phosphate, aluminum oxide, vitamin E acetate solubilisate, (mineral) oil emulsions, non-ionic detergents, squalene and saponins. Other adjuvants which may be used include an oil based adjuvants such as Freund's complete adjuvant (FCA), and Freund's incomplete adjuvant (FIA). Other adjuvants include cross-linked olefinically unsaturated carboxylic acid polymers, such as cross-linked acrylic acid polymers. As used herein the term "cross-linked acrylic acid polymer" refers to polymer and copolymers formed from a monomer mixture which includes acrylic acid as the predominant monomer in the mixture. Examples of suitable cross-linked acrylic acid polymers include those commercially available under the tradenames Carbopol® 934P and Carbopol® 971 (available from B.F. Goodrich Co., Cleveland, Ohio). Examples of suitable adjuvants include veterinarily accepted adjuvants.

It is generally advantageous to formulate the present compositions in dosage unit form for ease of administration and uniformity of dosage. "Dosage unit form" as used herein refers to physically discrete units suited as unitary dosages for the animal subjects to the treated; each unit containing a predetermined quantity of the active material calculated to produce the desired therapeutic or prophylactic effect in association with the required pharmaceutical carrier. The specification for the dosage unit forms are dictated by and depend on among other factors (a) the unique characteristics of the active material and the particular therapeutic or prophylactic effect to be achieved; (b) the limitations inherent in the art of compounding such active material for the treatment of disease; and (c) the manner of intended administration of the dosage unit form. In some embodiments, a dose of the immunogenic composition or vaccine includes at least about 10 micrograms (preferably 100 micrograms) of one or more isolated polypeptides or peptides as disclosed herein.

Sterile injectable solutions may be prepared by incorporating the isolated polypeptide or peptide in the desired amount in an appropriate solvent with various of the other ingredients enumerated above, as required, followed by filtered sterilization. Generally, dispersions can be prepared by incorporating the various active ingredients into a sterile vehicle which contains the basic dispersion medium and the required other ingredients from those enumerated above. In the case of sterile powders for the preparation of sterile injectable solutions, the preferred methods of preparation are vacuum-drying and the freeze-drying technique which yield a powder of the active ingredient (i.e., lyophilized form of the active ingredient) plus any additional desired ingredient from a previously sterile-filtered solution thereof.

It also may be advantageous to add a stabilizer to the present compositions. Suitable stabilizers include, for example, glycerol/EDTA, carbohydrates (such as sorbitol, mannitol, trehalose, starch, sucrose, dextran or glucose), proteins (such as albumin or casein) and protein degradation products (e.g., partially hydrolyzed gelatin). If desired, the formulation may be buffered by methods known in the art, using reagents such as alkali metal phosphates, e.g., sodium hydrogen phosphate, sodium dihydrogen phosphate, potassium hydrogen phosphate and/or potassium dihydrogen phosphate. Other solvents, such as ethanol or propylene glycol, can be used to increase solubility of ingredients in the vaccine formulation and/or the stability of the solution. Further additives which can be used in the present formulation include conventional antioxidants and conventional chelating agents, such as ethylenediamine tetraacetic acid (EDTA).

Also disclosed herein are isolated antisera, antibodies, or other binding molecules that specifically bind to the peptides disclosed herein. For example, the antisera, antibodies, or other binding molecules, may include an isolated antibody that specifically binds to a polypeptide consisting of an amino acid sequence of any of SEQ ID NOs:1-13. Preferably, the antisera, antibodies, or other binding molecules disclosed herein also bind specifically to sperm (e.g., canine sperm). The isolated antibody or binding molecule may be of any suitable isotype (e.g., IgG, IgM, IgE, IgD, IgA, and mixtures thereof). The antibodies may be polyclonal or monoclonal. The term "antibody or other binding molecule" refers to intact immunoglobulin molecules as well as to fragments thereof, such as Fab, F(ab')$_2$, and Fv fragments, which are capable of binding an epitopic determinant. The antibodies or other binding molecules may be naturally occurring or synthetic (e.g., scFv). Other binding molecules may include antibody fragments (e.g., Fab fragments), coupled antibodies, and coupled antibody fragments. Antibodies or other binding molecules that bind the presently disclosed peptides and polypeptides can be induced or elicited using the intact peptide or a polypeptide comprising the intact peptide as an immunizing antigen. The polypeptide or oligopeptide used to immunize an animal (e.g., a dog or other animal) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide may then be used to immunize the animal.

The peptides and polypeptides contemplated herein bind specifically to ZP. Furthermore, the peptides and polypeptides contemplated herein may be utilized in immunogenic compositions or vaccines for eliciting antibodies that bind specifically to sperm. The terms "specific binding" and "specifically binding" refer to that interaction between the polypeptide (or peptide) and the ZP; or to that interaction between sperm and an antibody (or other binding molecule). The interaction is dependent upon the presence of a particular structure of the protein, e.g., the antigenic determinant or epitope present on the polypeptide or peptide, recognized by the antibody or binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

Also disclosed herein are kits. The kits may include one or more components for performing the methods disclosed herein. For example, the kits may include one or more of the immunogenic compositions or vaccines disclosed herein for immunizing or vaccinating an animal, or the kits may include components for making the immunogenic compositions or vaccines as disclosed herein. The components may be provided in any suitable form (e.g., liquid form or lyophilized form).

EXAMPLES

The following EXAMPLES are illustrative and are not intended to limit the scope of the claimed subject matter.

Example 1

Methods, Compositions, and Sequences of ZP-Binding Peptides for Immunocontraception of Dogs and Other Animals Summary Zona pellucida (ZP) is a glyco-proteinaceous protective barrier surrounding all mammalian ova (eggs). Sperm must cross this barrier in order for fertilization and conception to occur, thus inhibition of sperm-zona interaction results in infertility. Peptides that recognize and bind to ZP were identified via selection from two phage display libraries (7- and 12-mer) using a novel procedure that utilizes intact oocytes surrounded by ZP proteins. The major advantage of this procedure is that ZP proteins are on oocytes in their native comformation unlike in previously published selection protocols on denatured ZPs immobilized on artificial solid support. Here, peptide/oligonucleotide sequences with proven binding specificity to canine ZP proteins were identified. Identified peptide sequences from phage display selection on intact dog oocytes surrounded by ZP included: LNSFLRS (SEQ ID NO:1), LSTALRS (SEQ ID NO:2), SSWYRGA (SEQ ID NO:3), TGTSTRA (SEQ ID NO:4), YLPIYTIPSMVY (SEQ ID NO:5), NNQSPILKLSIH (SEQ ID NO:6), and AHPNTAPIHPKF (SEQ ID NO:7). Based on the peptide sequences, the following five antigens were prepared: antigen 1—YLPVGGLRRIGG (SEQ ID NO:14), antigen 2—CLNSFLRSC-KGG (SEQ ID NO:9), antigen 3—YLPIYTIPSMVY-GG (SEQ ID NO:12), antigen 4—NNQSPILKLSIH-GG (SEQ ID NO:13), and antigen 5—CSSWYRGAC-KGGY (SEQ ID NO:11). Antigen 1 was used as a control (6). At least one of these antigens (antigen 4), when administered into dogs, resulted in generation of specific anti-peptide antibodies at high levels. Such antibodies can affect fertility, for example, via reduction of sperm motility, inhibition of acrosome reaction, and/or interference with sperm-oocyte interactions. Immunocontraceptive agents designed to include the identified sequences (for example, agents based on biological vectors such as bacterial and viral vectors) can be exploited for immunocontraception of dogs and/or other animals if peptides show interspecies properties. Additionally, preparations containing whole phage particles displaying ZP-binding peptides can be exploited for immunocontraception as well.

Introduction

Sperm antigens that are located on the surface of sperm can be used for contraceptive purposes (1,2,3,4). Sperm head antigens that bind to zona pellucida (ZP) are known to be involved in conception. Antibodies to sperm antigens have been found naturally in some males and females and frequently affect fertility (4). Such antibodies have the potential to be utilized for contraceptive purposes. Using phage display technology, others selected a human peptide that bound to the human sperm/egg interactive site (5) and used the peptide as an antigen to produce anti-sperm antibodies that prevented conception in mice (6,7).

Here, a novel procedure was developed for identification of ZP-binding peptides by selection from phage display libraries using intact oocytes surrounded by ZP proteins. In this procedure, ZP proteins remain on oocytes in their native conformation, unlike previously published selection protocols that use denatured ZPs immobilized on an artificial solid support. Using this novel selection procedure on intact oocytes surrounded by ZP proteins, a number of dog ZP-binding peptides were identified. Some of these peptides were used further to demonstrate their ability to produce anti-sperm antibodies. Such antibodies have the potential to affect fertility, for example, via reduction of sperm motility, inhibition of acrosome reaction, and/or interference with sperm-oocyte interactions.

Procedures and Results

Development of a procedure for selection of ZP-binding phage on intact oocytes: The zona pellucida (ZP) is a glycoproteinaceous protective barrier which surrounds mammalian ova. It is essential for sperm-egg interaction, since without this function, fertilization and conception cannot occur. Antibodies having specific epitopes which attach to functional sperm/ZP binding sites prevent fertility.

Here, phage display technology was utilized to identify antigens that may be utilized to effectively block fertility in dogs. In the art, phage display technology has resulted in the discovery of thousands of previously undetected binding proteins of enormous biological significance (14). Phage display libraries are heterogeneous mixtures of billions of phage clones, each of which expresses a different foreign DNA insert. Clones that bind to a given subject protein are easily separated from non-binding clones, allowing rapid identification of peptide ligands uniquely expressed by the bound phage. The complexity of phage display libraries and the existing wide diversity of these libraries provide virtually unlimited sources for finding desirable ligands/binding epitopes. The power of this technology is complemented by laboratory methods that make this technology technically uncomplicated and inexpensive (15).

The phage display methods disclosed here identified peptides that bind to ZP. These peptides may be utilized to induce antibodies that bind to sperm rather than to ZP proteins. Therefore, the induced antibodies can be considered "sperm antibodies" because peptide and sperm are equivalent with respect to binding with ZP. Vaccines that use ZP proteins as antigen are limited to immunizing females, while a vaccine based on ZP-binding peptides may induce antibodies that interfere with fertility of sperm in situ of immunized males, and may have the important advantage of being effective in both genders.

The phage display procedure developed herein utilizes intact oocytes surrounded by ZP proteins. In this procedure, ZP proteins remain on oocytes in their native conformation, unlike previously published selection protocols that use denatured ZPs immobilized on an artificial solid support. The procedure involves incubating isolated oocytes with a phage display library followed by washing of unbound phage. Oocytes are lysed, and bound phage are amplified in bacterial cultures. Enrichment in ZP-binding phage clones is achieved in four subsequent selection rounds, after which selected phage DNAs are sequenced and translated to obtain peptide sequences.

Figure 1:
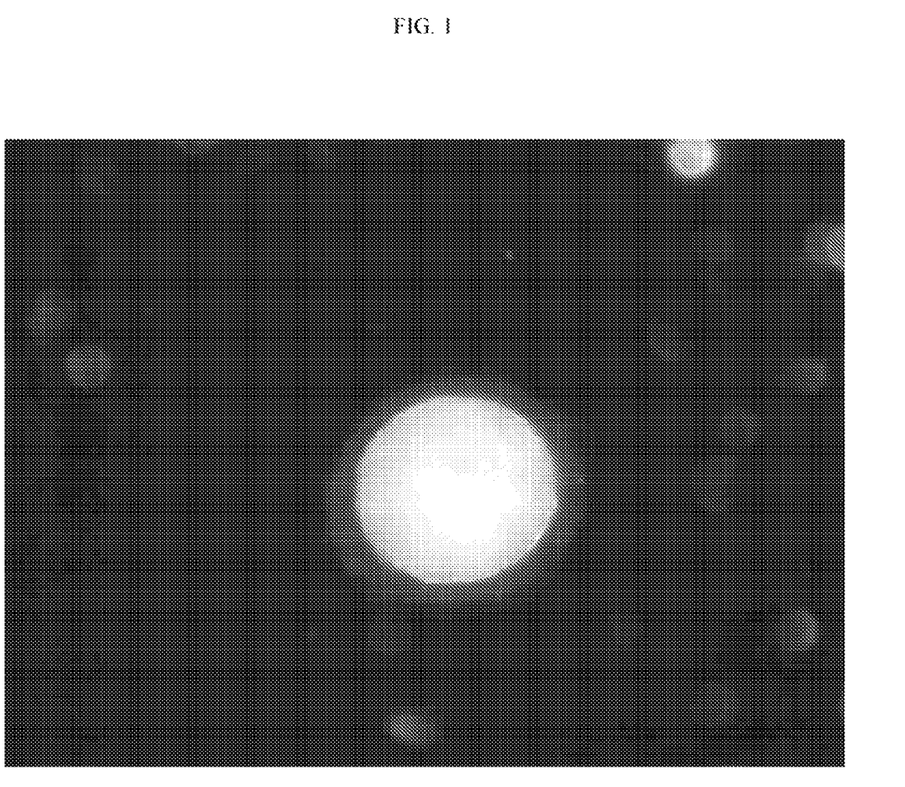
FIG. 1. Image of oocytes (obtained with dark-field microscope) from dog ovaries used in selection experiments for identification of ZP-binding peptides. A faint halo of ZP and a lack of cumulus cells were observed surrounding the ova.

Collection of dog ova: Oocytes were isolated from dog ovaries obtained from spay/neuter clinics. All ovaries were collected from bitches (six months of age and older) undergoing elective ovariohysterectomy. Approximately 20-30 oocytes from each pair of ovaries were isolated. Ova were washed extensively, retrieved by visual inspection at 12× magnification, washed two additional times, pooled and frozen before the use. Oocytes isolated from dog ovaries were characterized by microscopic evaluations. FIG. 1 shows a dark-field image of intact oocytes surrounded by zona pellucida. The oocytes did not have cumulus cells attached to the surface, making zona sites available for binding with phage in phage selection procedures.

Figure 2:
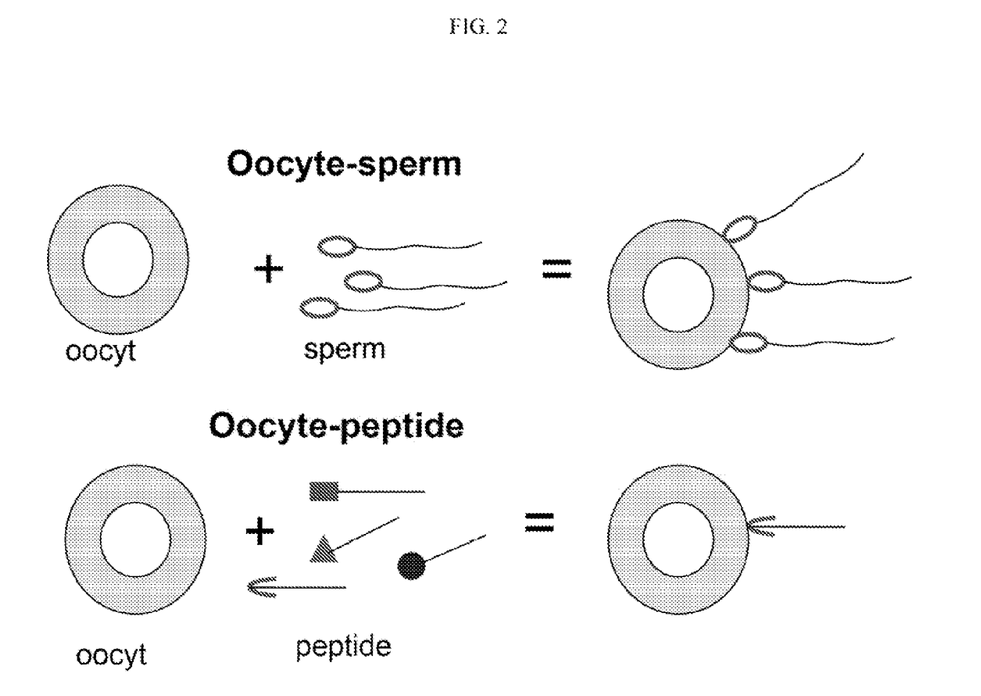
FIG. 2. Schematic representation of oocyte-sperm and oocyte-peptide binding. ZP-binding peptides are selected from a phage display library. ZP-binding peptides selected as such mimic ZP-binding peptides that are present on the surface of a sperm cell.

Identification of peptides that bind to ZP proteins on intact canine oocytes: Peptides that specifically bind to ZP proteins were identified by utilizing two phage display libraries purchased from New England BioLabs, including: PhD-C7C Peptide 7-mer Library Kit and PhD-12 Peptide Library Kit. The utilized approach selects peptides that mimic the sperm antigen at the level of the ZP-sperm binding (FIG. 2).

Four rounds of selection were performed using each library. For each selection round, an aliquot of the primary library was diluted in a blocking buffer and incubated with 1000 intact canine oocytes surrounded by ZP. After incubation, phages expressing peptides not bound to oocytes were washed away and the bound phages were recovered by lysis. Translation of foreign oligonucleotide inserts in phage DNA revealed sequences of the peptides that are responsible for binding to ZP. Peptide sequences from phage display selection on intact dog oocytes surrounded by ZP included: LNSFLRS (SEQ ID NO:1), LSTALRS (SEQ ID NO:2), SSWYRGA (SEQ ID NO:3), TGTSTRA (SEQ ID NO:4), YLPIYTIPSMVY (SEQ ID NO:5), NNQSPILKLSIH (SEQ ID NO:6), and AHPNTAPIHPKF (SEQ ID NO:7). Based on the peptide sequences, the following five antigens were prepared: antigen 1—YLPVGGLRRIGG (SEQ ID NO:14), antigen 2—CLNSFLRSC-KGG (SEQ ID NO:9), antigen 3—YLPIYTIPSMVY-GG (SEQ ID NO:12), antigen 4—NNQSPILKLSIH-GG (SEQ ID NO:13), and antigen 5—CSSWYRGAC-KGGY (SEQ ID NO:11).

Immunization of dogs with ZP-binding peptides conjugated to a carrier protein: The peptides were synthesized by Global Peptide Services (Fort Collins, Colo.) at a yield of 10-20 mg having 95% purity. Two of the selected peptides were 7 amino acids long and the other two were 12 amino acids long. Antigen was taken from the literature (6) to serve as a control. To assure maximum immunogenicity, the peptides were conjugated to keyhole-limpet hemocyanin (KLH), a carrier protein. For vaccinations, the antigen was formulated to include: 250 µg of KLH conjugated peptide mixed with aluminum hydroxide adjuvant (Alhydrogel 85) and 100 µg canine specific immunostimulatory oligodeoxynucleotide (CpG). Four of the selected peptides and one control peptide were injected intramuscularly into each dog (one dog/peptide). Booster immunizations were given twice to achieve high titer antisera. Each immunized dog served as his/her own control since none were expected to have preexisting antibodies to the selected peptides. Immunizations did not result in any adverse reactions in any of the dogs.

Figure 3:
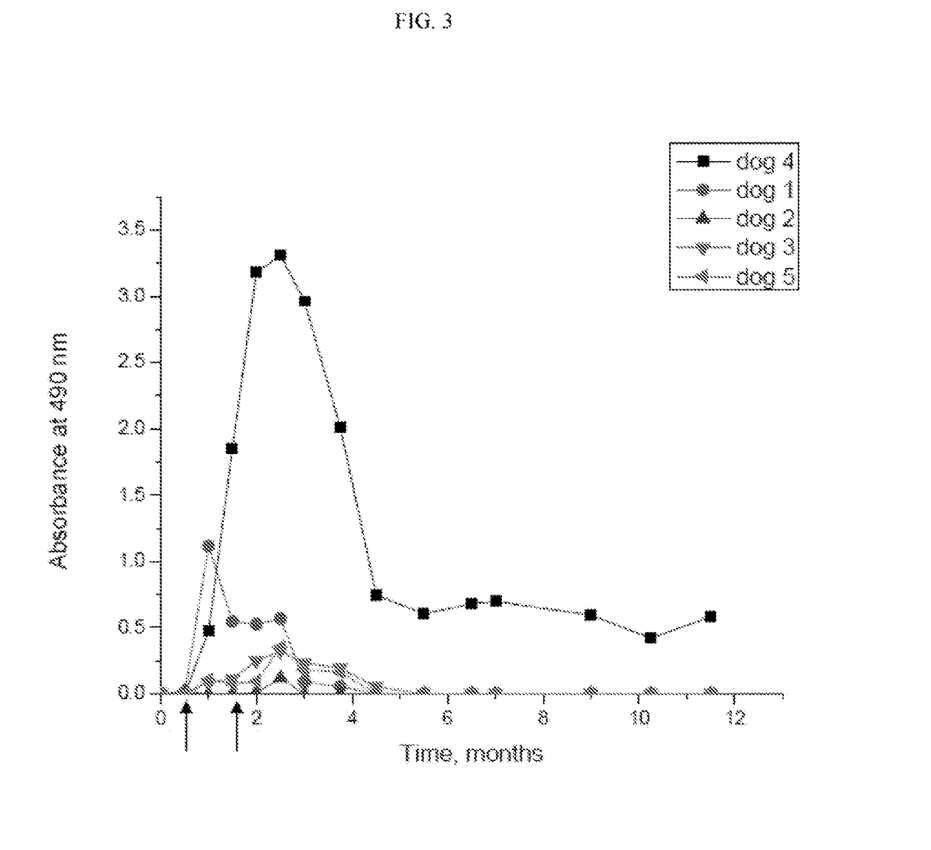
FIG. 3. Anti-peptide antibody levels in serum samples collected from dogs immunized with five different ZP-binding peptide antigens (one dog per antigen). The data were obtained by ELISA at serum dilution 1:6400. Arrows indicate time of boosts.
Figure 4:
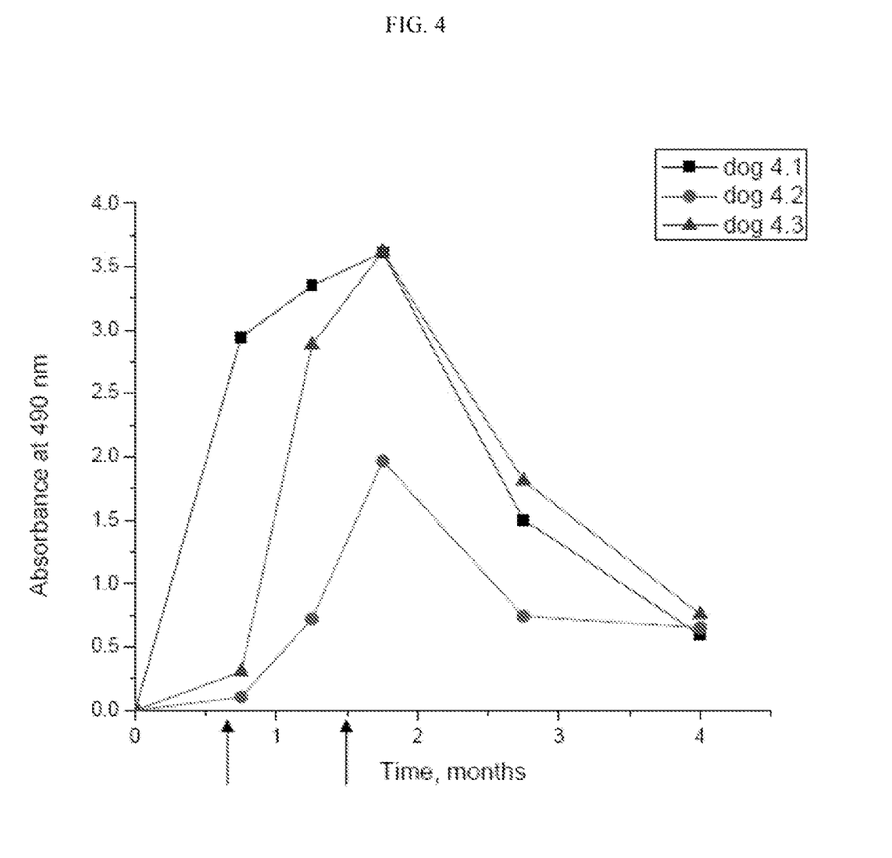
FIG. 4. Anti-peptide antibody levels in serum samples collected from three dogs immunized with ZP-binding peptide antigen 4. The data were obtained by ELISA at serum dilution 1:6400. Arrows indicate time of boosts.
Figure 5:
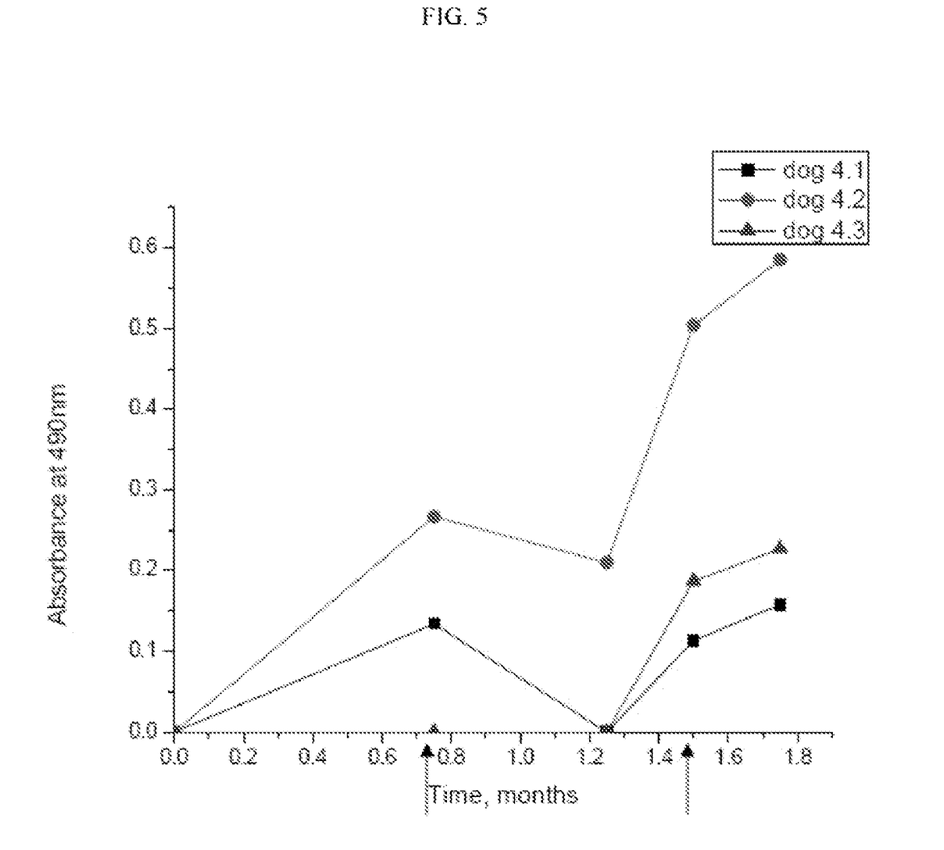
FIG. 5. Anti-sperm antibody levels in serum samples collected from three dogs immunized with ZP-binding peptide antigen 4. The data were obtained by ELISA at serum dilution 1:50. Arrows indicate time of boosts.

Evaluation of serum collected from immunized dogs for anti-ZP-binding peptide antibodies: Serum samples were collected from all dogs prior to immunization and biweekly or monthly thereafter during a 12-month period. The samples were tested for the presence of anti-peptide antibodies in a peptide ELISA format. Based on ELISA tests, out of four selected peptides, one peptide demonstrated high immunogenicity, two peptides demonstrated moderate to low immunogenicity and one peptide was not immunogenic (FIG. 3). The peptide with high immunogenic properties (antigen 4) was tested further in three additional dogs. The immunization scheme was as described above. All dogs immunized with this peptide showed high titers of anti-peptide antibodies (FIG. 4). In addition to the ELISA tests that demonstrated high immunogenicity of the peptide antigen 4, studies in a sperm cell ELISA format were performed. The results have indicated that the antibodies raised against the highly immunogenic peptide 4 bind to canine sperm cells, suggesting they may act as anti-sperm antibodies (FIG. 5).

Additional Assays

Phage block ZP/sperm interaction: Early confirmation of the ability of selected peptide, in the context of phage expressing the peptide, to functionally block sperm/ZP interaction improves efficiency and economy of the assessment process. Therefore, the ability of phage expressing the identified peptides to exclude normal dog sperm binding may be assessed. The method of Hay (28) using the fluorescent nuclear label Hoechst 33258 (Sigma) to visualize sperm may be used. Untreated ova exposed to normal sperm may serve as controls.

Sperm/ZP Binding Assay: The ability of sperm to penetrate and bind ZP in the presence of anti-peptide antibody may be assessed using an assay of Hay et al. (28). This assay tests the ability of sperm to penetrate and bind ZP of immunized bitches. This assay also tests the ability of sperm treated with anti-cZP binding peptide antibodies versus normal sperm to penetrate and bind to normal canine ZP. The interaction of normal sperm and oocytes may be used as a positive control. Briefly, normal fresh canine ovaries collected after routine ovariohysterectomies are sliced in PBS to release oocytes. Selected oocytes have uniformly dark ooplasm, an intact cumulus cell complex, and no apparent irregularities in the ZP (29). Oocytes are washed in PBS, then IVF medium, transferred to droplets of medium which are over-layed with conditioned silicone oil, then incubated for 1-3 hrs in humidified 5% $CO_2$ atmosphere at 38° C. Fresh normal dog sperm is washed and resuspended in canine sperm capacitation medium and checked for motility and concentration. Samples are diluted to a concentration of $40 \times 10^5$ motile sperm/ml. Five µl of sperm suspension are added to droplets containing ova to a final concentration of $2 \times 10$ motile sperm/ml. After 16-18 hr incubation in a humidified atmosphere (5% $CO_2$, 38° C.), oocytes are washed and transferred into 1 ml of 1% Na citrate for 10 min. Oocytes are then transferred to a microcentrifuge tube (1.5 ml) with 200 µl Na-citrate and stripped of cumulus cells and loosely bound sperm by vortexing for 3 min. The oocytes are then recovered and incubated for 20 min in 1 ml PHS containing 100 µl of the fluorescent nuclear label Hoechst 33258 (Sigma) to visualize sperm. Following staining, oocytes are washed and mounted on glass slides with coverslips supported by petroleum jelly containing 200 micron beads. Oocyes are examined under fluorescent microscopy to count percent of ova containing penetrated sperm, and the number of sperm penetrated per ova. The same protocol is used to test penetration and binding of sperm reacted with anti-peptide antibody to normal oocytes, normal sperm penetration and binding to oocytes reacted with anti-peptide antibody in vitro, and normal sperm penetration and binding of oocytes from immunized bitches.

Species specificity of fertility block: There are well documented species differences in the ability of anti-ZP antibodies generated in one species (e.g., porcine ZP) to block fertility in other species. Therefore, it may be possible that the anti-canine sperm antibodies disclosed herein also may interfere with fertility in other species, such as mice and cats. For example, Naz, et al. observed that human-specific peptide used to immunize mice induced infertility in that species also (7). If the canine-specific antigen also blocks fertility in mice, this opens the opportunity to use mice as an experimental model for preliminary functional assessment of our selected peptides. Therefore, Balbc (Jax Labs, Bar Harbor, Me.) mice may be used to determine if: (1) canine peptides bind to mouse ova in vitro, (2) female mice immunized with canine peptide generate antibodies which react with mouse ova in situ, and (3) female mice immunized with canine peptide antigen become infertile. These experiments may use methods described here or described by Naz et al. and Millar et al. (mouse infertility test) (7, 26). The test species range of canine reactive peptides also may be tested in an in vitro reaction with feline ova.

Anti-cZP binding site antibody interaction with normal canine sperm and oocytes: To confirm anti-peptide antibody/sperm interaction and subcellular localization of the binding site, normal canine sperm may be collected, fixed in methanol, reacted with this antibody, stained with fluorescein isothiocyanate labelled goat anti-canine IgG, and examined using immunofluorescence. Untreated normal canine serum may be used as a control. Anti-peptide antibodies should bind at the acrosomal region. Since the sperm/zona binding site is presumed to be a lock and key mechanism, anti-peptide antibody should react with sperm, while peptide should not. Similar immunofluorescence examination of normal and immunized ovaries may be performed to examine for anti-peptide binding of zona in situ (27).

REFERENCES FOR EXAMPLE 1

1. Suri A. Sperm-based contraceptive vaccines: current status, merits and development. Expert Rev Mol Med. 2005 Sep. 12; 7(18):1-16.
2. Suri A. Contraceptive vaccines targeting sperm. Expert Opin Biol Ther. 2005 March; 5(3):381-92.
3. Naz R K, Gupta S K, Gupta J C, Vyas H K, Talwar A G. Recent advances in contraceptive vaccine development: a mini-review. Hum Reprod 2005; 20(12):3271-3283.
4. Chamley L W, Clarke G N. Antisperm antibodies and conception. Semin Immunopathol 2007; 29(2):169-184.
5. Naz R, Zhu X, Kadam A. Identification of human sperm peptide sequence involved in egg binding for immunocontraception. Biology of Reproduction 2000; 62:318-324.
6. Naz R K, Chauhan S C. Human sperm-specific peptide vaccine that causes long-term reversible contraception. Biol Reprod. 2002 August; 67(2):674-80.
7. Naz R. Human Synthetic peptide vaccine for contraception targeting sperm. Archives of Andrology 2004; 50:113-119.
8. Brown, R. G., Kimmins, W. C., Mezei, M., Parsons, J., Pohajdak, B., and Bowen, W. D. A single administration immunocontraceptive vaccine for grey seals. Nature 379: 30-31, 1996.
9. Fayrer-Hosken R A, Grobler D, Van Altena J J, Bertschinger H J and Kirkpatrick J F Immunocontraception of African elephants. Nature 407: 149, 2000.
10. Patterson M, Jennings Z A, van Duin M, Aitken R J. Immunocontraception with zona pellucida proteins. Cells Tissues Organs. 166: 228-232, 2000.
11. Whier, H. Immuno-sterilization in dogs using zona pellucida based vaccines. Proceedings of the Symposium on Nonsurgical Methods for Pet Population Control, Breckenridge, Colo., Jun. 24-27, 2004.
12. Harris J. Swine Z P and dog immunocontraception. Proceedings of the Symposium on Nonsurgical Methods for Pet Population Control, Breckenridge, Colo., Jun. 24-27, 2004.
13. Jewgenow K, Greube A, Naidenko S and Ringleb J. Antigenic and antifertility determinants of feline zona pellucida Protein—A strategy for contraceptive vaccine development. Proceedings of the Symposium on Nonsurgical Methods for Pet Population Control, Breckenridge, Colo., Jun. 24-27, 2004.
14. Kehoe J W and B K Kay. Filamentous Phage Display in the New Millenium. Chem. Rev., 105, 4056-4072, 2005.

15. Samoylova T. I., and Smith B. F. Identification of cell targeting ligands using random peptide presenting phaga libraries. In Genetic Library Construction and Screening. Advanced Techniques and Applications. C. Bird and B. Smith, eds., Springer-Verlag, Heidelberg, pp. 209 231, 2002.
16. Samoylova T I, Ahmed B Y, Vodyanoy V, Morrison N E, Samoylov A M, Globa L P, Baker H J, and Cox N R. Targeting peptides for microglia identified via phage display. J. Neuroimmunology, 127:13-21, 2002.
17. Baker H J and Griffin B. "Immunization of Cats and Dogs with an Anti-GnRH Protein Vaccine with Molecular Adjuvantation". Proceedings of the Symposium on Nonsurgical Methods for Pet Population Control, Breckemidge, Colo., Jun. 24-27, 2004.
18. Wernette C M, Smith B F, Barksdale Z, Hecker R and Baker H I CpG oligodeoxynucleotides stimulate canine and feline immune cell proliferation. Veterinary Immunology and Immunopathology 2002; 84: 223-236.
19. Fang J, Wang G, Yang Q, Song J, Wang Y, Wang L. The potential of phage display virions expressing malignant tumor specific antigen MAGE-A1 epitope in murine model. Vaccine, 23(40):4860-6, 2005.
20. Gaubin M, Fanutti C, Mishal Z, Durrbach A, De Berardinis P, Sartorius R, Del Pozzo O, Guardiola J, Perham R N, Piatier-Tonneau D. Processing of filamentous bacteriophage virions in antigen-presenting cells targets both HLA class I and class II peptide loading compartments. DNA Cell Biol, 22(1):11-8, 2003.
21. Yip Y L, Smith G, Ward R L. Comparison of phage pill, pVUI and OST as carrier proteins for peptide immunisation in Balb/c mice. Immunol Lett Dee 3; 79(3): 197-202, 2005.
22. Dunbar B S, Wardrip N J and Hedrick J L. Isolation, physiochemical properties and macromolecular composition of zona pellucida from porcine oocytes. Biochemistry 19, 1980: 356-365.
23. Matsuo H, Baba, Y, Nair R M G. Arimuta A, Schally A V. Codon usage bias for the domestic dog. Biochemical Biophysical Research Communications. 1971; 43. 1334.
24. Smith O P, Filamentous fusion phage: novel expression vectors that display clined antigens on the virion surface. Science 1985, 228: 1315-1317.
25. Barbas C F III, Burton D R. Scott J K and G J Silverman. 2001. Phage Display: A Laboratory Manual. Cold Spring Harbor Laboratory Press, Cold Spring Harbor, N.Y.
26. Millar S E, Chamow S M, Baur A W, Oliver C, Robey F, Dean J: Vaccination with a synthetic zona pellucida peptide produces long-term contraception in female mice. Science. 1989; 246: 935-938.
27. Inauova M, Mollova M, Ivanova Kicbeva M G, Petrov M, Djarkova T, Somlev B. Effect of cryopreservation of zona-binding capacity of canine spermatozoa in vitro. Theriogenology 1999; 52:163-170.
28. Hay M A, King W A, Gartley C J Leivo, S P and Goodrowe 1 (L. Canine spermatozoa croyopreservation and evaluation of gamete interaction. Theriogenology 48: 1329-1342, 1997.
29. Mastromonaco G F, Hay M A and Goodrowe K L. The effects of oocyte storage and cumulus cell presence on canine zona penetration by domestic dog spermatozoa. Theriogenology 57: 1123-1134, 2002.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

In addition, where features or aspects of the invention are described in terms of Markush groups or other grouping of alternatives, those skilled in the art will recognize that the invention is also thereby described in terms of any individual member, any subgroup of members of the Markush group or other group, or the totality of members of the Markush group or other group.

Citations to a number of patent and non-patent references are made herein. The cited references are incorporated by reference herein in their entireties.

We claim:

1. A method for identifying a peptide that binds to intact oocytes, the method comprising
   (a) isolating intact oocytes;
   (b) contacting no more than 1000 of the intact oocytes with a phage library;
   (c) selecting phage that bind to the intact oocytes, thereby identifying peptides that bind to the intact oocytes.

2. The method of claim 1, wherein the intact oocytes are intact canine oocytes.

3. The method of claim 1, wherein the intact oocytes comprise a zona pellucida.

4. The method of claim 1, wherein the intact oocytes comprise zona pellucida proteins in their native conformation.

5. The method of claim 1, wherein the method comprises removing phage expressing peptides not bound to the intact oocytes after (b).

6. The method of claim 1, wherein selecting phage that bind to the intact oocytes comprises recovering bound phage by lysing the intact oocytes.

7. The method of claim 1, wherein the method comprises four rounds of contacting and selecting.

8. The method of claim 1, wherein the phage library comprises phage expressing 7-mer peptides.

9. The method of claim 1, wherein the phage library comprises phage expressing 12-mer peptides.

* * * * *

SEQUENCE LISTING

```
<160> NUMBER OF SEQ ID NOS: 14

<210> SEQ ID NO 1
<211> LENGTH: 7
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(7)

<400> SEQUENCE: 1

Leu Asn Ser Phe Leu Arg Ser
1               5

<210> SEQ ID NO 2
```

```
<211> LENGTH: 7
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(7)

<400> SEQUENCE: 2

Leu Ser Thr Ala Leu Arg Ser
1               5

<210> SEQ ID NO 3
<211> LENGTH: 7
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(7)

<400> SEQUENCE: 3

Ser Ser Trp Tyr Arg Gly Ala
1               5

<210> SEQ ID NO 4
<211> LENGTH: 7
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(7)

<400> SEQUENCE: 4

Thr Gly Thr Ser Thr Arg Ala
1               5

<210> SEQ ID NO 5
<211> LENGTH: 12
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(12)

<400> SEQUENCE: 5

Tyr Leu Pro Ile Tyr Thr Ile Pro Ser Met Val Tyr
1               5                   10

<210> SEQ ID NO 6
<211> LENGTH: 12
<212> TYPE: PRT
<213> ORGANISM: Artificial
<220> FEATURE:
<223> OTHER INFORMATION: Phage library random peptide insert
<220> FEATURE:
<221> NAME/KEY: Peptide
<222> LOCATION: (1)..(12)

<400> SEQUENCE: 6

Asn Asn Gln Ser Pro Ile Leu Lys Leu Ser Ile His
1               5                   10

<210> SEQ ID NO 7
```

```
<211> LENGTH: 12
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(12)

<400> SEQUENCE: 7

Ala His Pro Asn Thr Ala Pro Ile His Pro Lys Phe
1               5                   10

<210> SEQ ID NO 8
<211> LENGTH: 9
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(9)

<400> SEQUENCE: 8

Cys Leu Asn Ser Phe Leu Arg Ser Cys
1               5

<210> SEQ ID NO 9
<211> LENGTH: 12
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(12)

<400> SEQUENCE: 9

Cys Leu Asn Ser Phe Leu Arg Ser Cys Lys Gly Gly
1               5                   10

<210> SEQ ID NO 10
<211> LENGTH: 9
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(9)

<400> SEQUENCE: 10

Cys Ser Ser Trp Tyr Arg Gly Ala Cys
1               5

<210> SEQ ID NO 11
<211> LENGTH: 13
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(13)

<400> SEQUENCE: 11

Cys Ser Ser Trp Tyr Arg Gly Ala Cys Lys Gly Gly Tyr
1               5                   10

<210> SEQ ID NO 12
```

-continued

```
<211> LENGTH: 14
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(14)

<400> SEQUENCE: 12

Tyr Leu Pro Ile Tyr Thr Ile Pro Ser Met Val Tyr Gly Gly
1               5                   10

<210> SEQ ID NO 13
<211> LENGTH: 14
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(14)

<400> SEQUENCE: 13

Asn Asn Gln Ser Pro Ile Leu Lys Leu Ser Ile His Gly Gly
1               5                   10

<210> SEQ ID NO 14
<211> LENGTH: 12
<212> TYPE: PRT
<213> ORGANISM: Artificial
<220> FEATURE:
<223> OTHER INFORMATION: Phage library random peptide insert
<220> FEATURE:
<221> NAME/KEY: PEPTIDE
<222> LOCATION: (1)..(12)

<400> SEQUENCE: 14

Tyr Leu Pro Val Gly Gly Leu Arg Arg Ile Gly Gly
1               5                   10
```